(12) United States Patent
Palumbo

(10) Patent No.: US 11,471,452 B2
(45) Date of Patent: *Oct. 18, 2022

(54) COMPOSITIONS AND METHODS FOR TREATING OR PREVENTING VASOMOTOR SYMPTOMS

(71) Applicant: Mitsubishi Tanabe Pharma Corporation, Osaka (JP)

(72) Inventor: Joseph M. Palumbo, Jersey City, NJ (US)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 7 days.

This patent is subject to a terminal disclaimer.

(21) Appl. No.: 15/733,253

(22) PCT Filed: Dec. 18, 2018

(86) PCT No.: PCT/JP2018/046544
§ 371 (c)(1),
(2) Date: Jun. 17, 2020

(87) PCT Pub. No.: WO2019/124366
PCT Pub. Date: Jun. 27, 2019

(65) Prior Publication Data
US 2020/0383968 A1    Dec. 10, 2020

Related U.S. Application Data

(60) Provisional application No. 62/607,666, filed on Dec. 19, 2017.

(51) Int. Cl.
*A61K 31/472* (2006.01)
*A61P 15/12* (2006.01)
*A61K 45/06* (2006.01)

(52) U.S. Cl.
CPC .......... *A61K 31/472* (2013.01); *A61K 45/06* (2013.01); *A61P 15/12* (2018.01)

(58) Field of Classification Search
CPC ........ A61K 31/472; A61K 45/06; A61P 15/12
See application file for complete search history.

(56) References Cited

U.S. PATENT DOCUMENTS 8,987,445 B2   3/2015   Tsuzuki et al.
10,993,939 B2  5/2021   Palumbo
(Continued)

FOREIGN PATENT DOCUMENTS

WO   WO-2012124825 A1 *  9/2012   ............. A61P 13/08
WO   WO 2017/217351 A1   12/2017

OTHER PUBLICATIONS

R. E. Williams et al., "Frequency and severity of vasomotor symptoms among peri- and postmenopausal women in the United States," Climacteric, 11:32-43 (2008).
(Continued)

*Primary Examiner* — San Ming R Hui
(74) *Attorney, Agent, or Firm* — Finnegan, Henderson, Farabow, Garrett & Dunner, LLP

(57) ABSTRACT

The present disclosure is directed to compositions comprising as an active ingredient, a lower dose of 4-({(4-cyclopropylisoquinolin-3-yl)[4-(trifluoromethoxy)benzyl]amino}sulfonyl)benzoic acid or a pharmaceutically acceptable salt thereof for treating or preventing vasomotor symptoms in a subject, and methods which comprises administering the said compound or the pharmaceutically acceptable salt thereof at a lower dose, respectively.

24 Claims, 6 Drawing Sheets

(56) References Cited

U.S. PATENT DOCUMENTS

| | | | |
|---|---|---|---|
| 2013/0157996 A1* | 6/2013 | Biswas | A61P 43/00 514/210.18 |
| 2015/0307454 A1 | 10/2015 | Kato et al. | |
| 2021/0177830 A1 | 6/2021 | Palumbo | |

OTHER PUBLICATIONS

Laura J. Hanisch et al., "Increases in core body temperature precede hot flashes in a prostate cancer patient," Psycho-Oncology, 18:564-567 (2009).

Karen Elkind-Hirsch, "Cooling off hot flashes: uncoupling of the circadian pattern of core body temperature and hot flash frequency in breast cancer survivors," Menopause: The Journal of The North American Menopause Society, vol. 11, No. 4, pp. 369-371 (2004).

Hadine Joffe et al., "A Gonadotropin-Releasing Hormone Agonist Model Demonstrates That Nocturnal Hot Flashes Interrupt Objective Sleep," Sleep, vol. 36, No. 12, pp. 1977-1985 (2013).

Naseem A. Aziz, "Evaluation of Core and Surface Body Temperatures, Prevalence, Onset, Duration and Severity of Hot Flashes in Men after Bilateral Orchidectomy for Prostate Cancer," Int. Braz. J. Urol., 34:15-22 (2008).

Hot flushes in a male population aged 55, 65, and 75 years, living in the community of Linköping, Sweden. Menopause. vol. 10, No. 1, pp. 81-87 (2003).

International Preliminary Report on Patentability dated Jun. 23, 2020, in International Patent Application No. PCT/JP2018/046544.

M.C. Almeida et al., "Pharmacological Blockade of the Cold Receptor TRPM8 Attenuates Autonomic and Behavioral Cold Defenses and Decreases Deep Body Temperature," The Journal of Neuroscience, vol. 32, No. 6, pp. 2086-2099, Feb. 8, 2012.

McKemy DD et al., "Identification of a cold receptor reveals a general role for TRP channels in thermosensation," Nature, MacMillian Journals Ltd, London, vol. 416, pp. 52-58, Jan. 1, 2002.

International Search Report, from International Patent Application No. PCT/JP2018/046544, dated Mar. 27, 2019.

Russian Office Action dated May 31, 2022, with English translation.

Russian Search Report dated May 31, 2022.

D2: S. M. Keh, et al. "The menthol and cold sensation receptor TRPM8 in normal human nasal mucosa and rhinitis," Rhinology, 2011, 49(4), p. 453-457—CTP. 455.

\* cited by examiner

[Fig. 1]
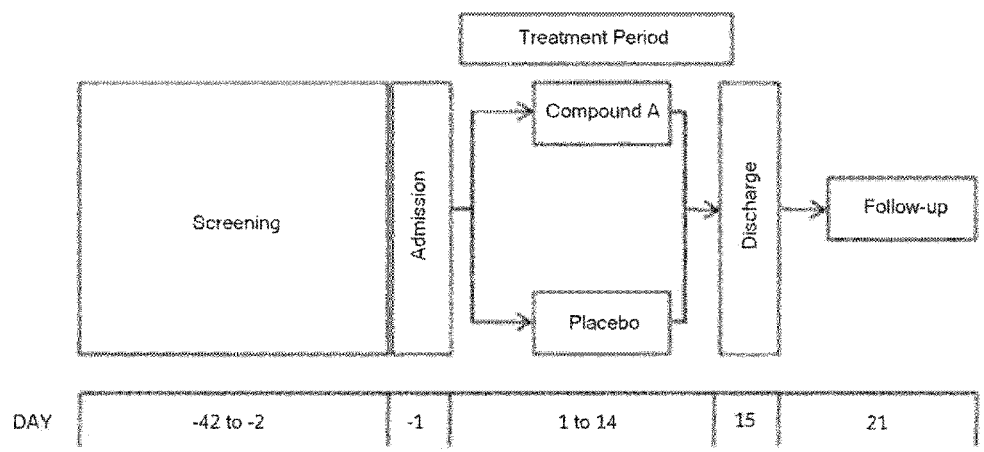
[Fig. 2]
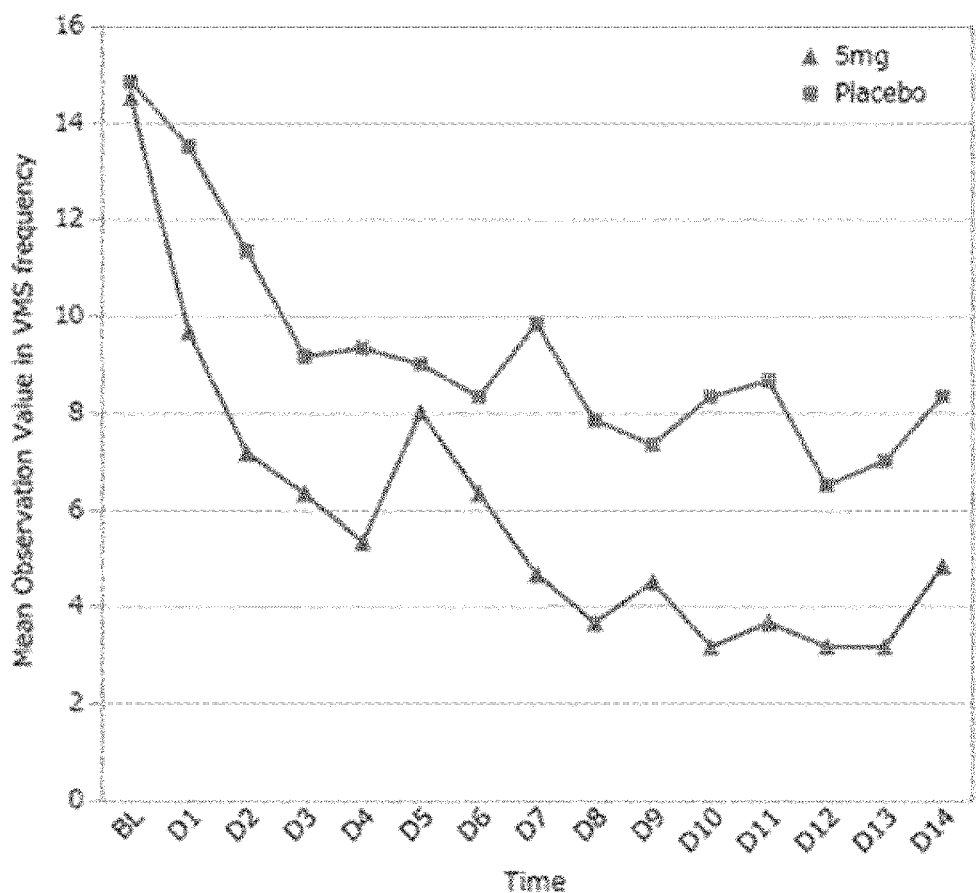

[Fig. 3]

Placebo group

5mg administered group

[Fig. 4]

20mg administered group

50mg administered group

[Fig. 5]
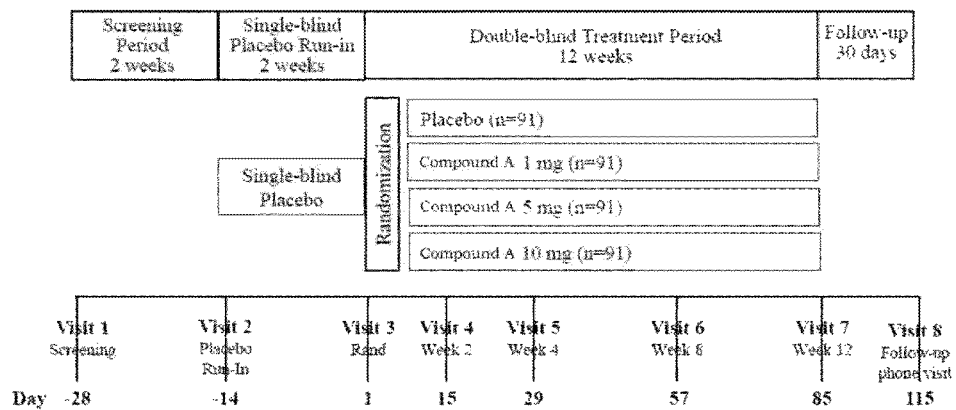
[Fig. 6]
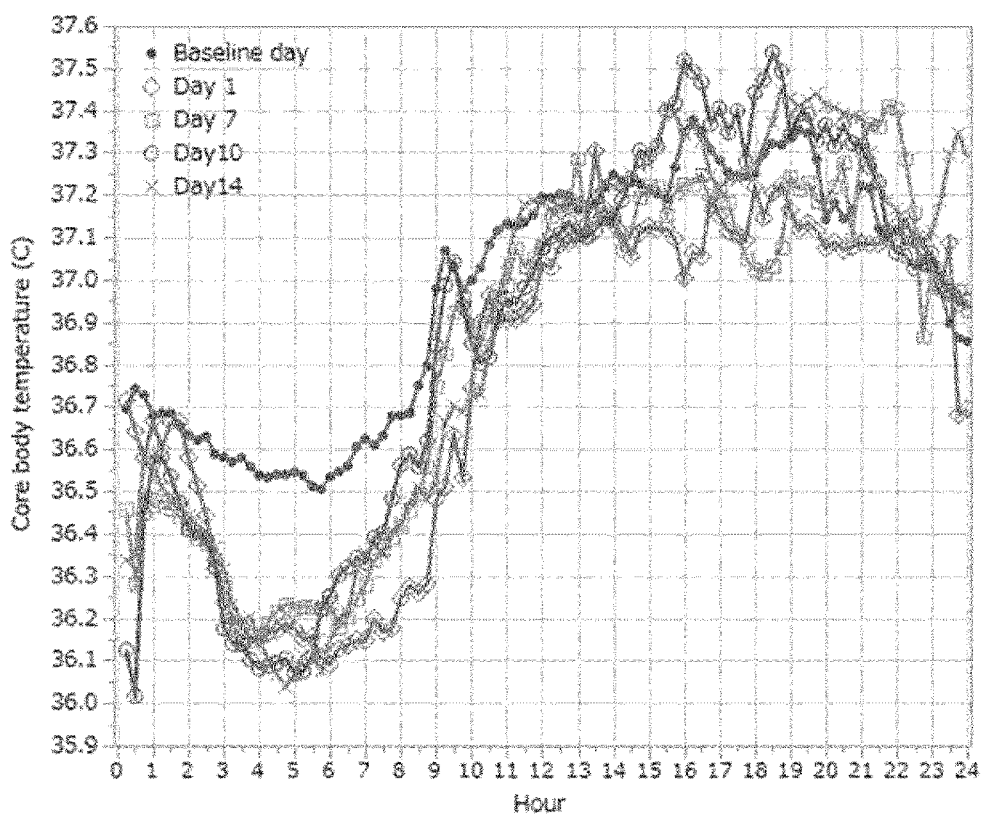

[Fig. 7]
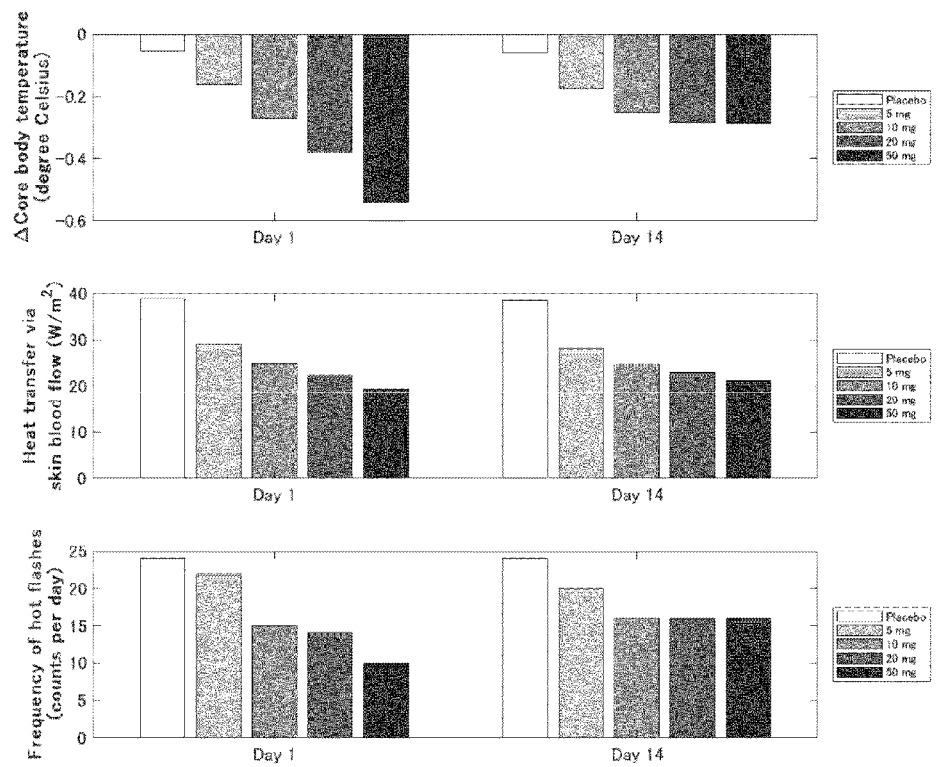

[Fig. 8]
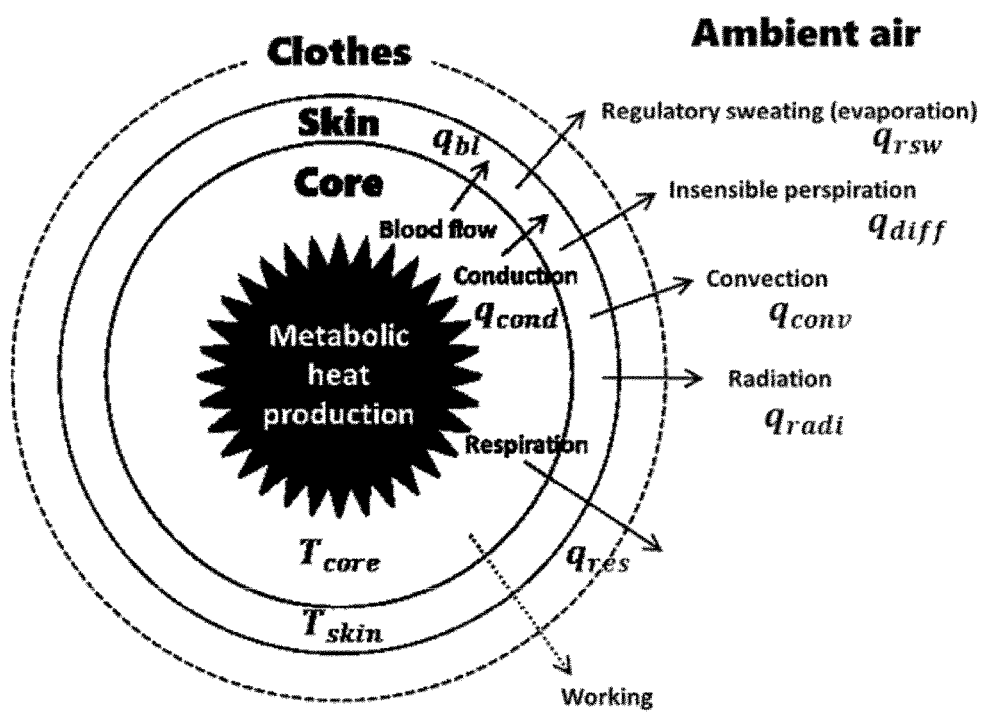

COMPOSITIONS AND METHODS FOR TREATING OR PREVENTING VASOMOTOR SYMPTOMS

This application is a national phase application under 35 U.S.C. § 371 based on International Application No. PCT/JP2018/046544, filed Dec. 18, 2018, and claims priority of U.S. Patent Application No. 62/607,666, filed Dec. 19, 2017; the contents of each application is incorporated herein by reference.

TECHNICAL FIELD

The present disclosure is directed to compositions comprising as an active ingredient, a lower dose of 4-({(4-cyclopropylisoquinolin-3-yl)[4-(trifluoromethoxy)benzyl]amino}sulfonyl)benzoic acid or a pharmaceutically acceptable salt thereof for treating or preventing vasomotor symptoms in a subject, and methods which comprises administering the said compound or the pharmaceutically acceptable salt thereof at a lower dose, respectively.

BACKGROUND ART

Vasomotor symptoms are commonly reported, e.g., symptoms of menopause. Vasomotor symptoms include night sweats, hot flashes, and flushes. The major and most common vasomotor symptoms are hot flashes. In general, hot flashes (or hot flushes or night sweats) are intermittent episodes of heat sensation. Hot flashes are the most common symptoms experienced by women who are perimenopausal or postmenopausal and are also commonly experienced by men and women who are undergoing or have undergone treatment for cancer, for example, patients receiving a breast or prostate cancer treatment that inhibits the production or activity of sex hormones. See Non-Patent Literatures 1 and 2. Studies suggest that hot flashes may be preceded by a rise in core body temperature. See Non-Patent Literature 3.

Episodes of vasomotor symptoms may also be associated with perspiration, flushing, chills, anxiety, and heart palpitations. For example, symptoms of hot flashes include a sudden sensation of warmth, often accompanied by one or more of sweating, skin reddening or flushing, and sensations of clamminess and chills. Hot flashes can be characterized by brief, mild warmth to waves of heat and profuse sweating. Typical hot flashes occur with sudden onsets of sensation of warmth in the chest, which then spreads upward to involve the neck and face and may also spread throughout the body. Others may feel a sudden onset of warmth all over the upper part of the body. Hot flashes may also be accompanied by dizziness, nausea, headaches, and palpitations. Hot flashes accompanied with sweating can also occur at night. These are called night sweats and have been linked to chronic insomnia and poor subjective sleep quality. See Non-Patent Literature 4. Recent polysomnography studies have determined that hot flashes occurring at night correlate with increased sleep fragmentation, which can result in, e.g., sleep deprivation, fatigue, and irritability. Thus, hot flashes can disrupt sleep and work and interfere with quality of life.

The severity of vasomotor symptoms varies from person to person and from time to time in the same person. For example, hot flashes can be provoked by several factors, such as hot weather, stress, eating, drinking alcohol, hormone changes, a medical condition, or medical treatment. Episodes can last from a few seconds to several minutes or in rarer cases up to an hour or more. Vasomotor symptoms can occur from several times a year to several times a week to as frequently as one or more per hour.

Hot flashes have been studied extensively in perimenopausal and postmenopausal women. Studies have shown that about 60% to 80% of women experience hot flashes in the period within peri- and postmenopause. Within this population, 40% to 60% report moderate-to-severe hot flashes, and 10% to 20% find them nearly intolerable. Thus, there is a need for effectively treating or preventing vasomotor symptoms (e.g., hot flashes) to maintain the quality of life of many women.

Vasomotor symptoms may also be experienced by both men and women as a symptom of a medical condition or a symptom of treatment. For example, vasomotor symptoms are experienced by many cancer patients as a symptom of the cancer or a symptom of the cancer treatment.

For instance, men with prostate cancer who undergo androgen deprivation therapy (ADT) may have hot flashes. This is a major quality of life issue for a significant proportion of men receiving ADT. It has been reported that about 40% to 80% of such men suffer hot flashes and 30% to 40% report major discomfort during such episodes. See Non-Patent Literature 5.

Further, it is also possible for men, in the process of aging, to spontaneously experience bothersome hot flashes. A 2003 study of 1.885 Swedish men, aged 55, 65, and 75 years, revealed that approximately one third of these men experience hot flashes, and that half of those men found the symptoms to be bothersome. See Non-Patent Literature 6.

There are several known treatments for vasomotor symptoms; however, current treatments are not completely effective and may confer increased risk of serious complications. Although estrogen replacement therapy can effectively minimize or prevent vasomotor symptoms in women, many women are concerned about potential risks of hormone replacement therapy. This is especially true for women who suffer from breast cancer or have a family history of breast cancer, and/or a history of clotting disorders. Selective serotonin reuptake inhibitors (SSRIs), serotonin and norepinephrine reuptake inhibitors (SNRIs), gabapentin and clonidine may also be used for the treatment of vasomotor symptoms, but are not always effective at treating symptoms and many are associated with unwanted side effects.

CITATION LIST

Non Patent Literature

[NPL 1] R. E. Williams et al., "Frequency and severity of vasomotor symptoms among peri- and postmenopausal women in the United States," Climacteric, 11:32-43 (2008)

[NPL 2] Laura J. Hanisch et al., "Increases in core body temperature precede hot flashes in a prostate cancer patient," Psycho-Oncology, 18:564-567 (2009)

[NPL 3] Karen Elkind-Hirsch, "Cooling off hot flashes: uncoupling of the circadian pattern of core body temperature and hot flash frequency in breast cancer survivors," Menopause: The Journal of The North American Menopause Society, Vol. 11, No. 4, pp. 369-371 (2004)

[NPL 4] Hadine Joffe et al., "A Gonadotropin-Releasing Hormone Agonist Model Demonstrates That Nocturnal Hot Flashes Interrupt Objective Sleep," Sleep, Vol. 36, No. 12, pp. 1977-1985 (2013).

[NPL 5] Naseem A. Aziz, "Evaluation of Core and Surface Body Temperatures, Prevalence, Onset, Duration and Severity of Hot Flashes in Men after Bilateral Orchidectomy for Prostate Cancer," Int. Braz. J. Urol., 34:15-22 (2008).

[NPL 6] Hot flushes in a male population aged 55, 65, and 75 years, living in the community of Linkoeping, Sweden. Menopause. Vol. 10, No. 1, pp. 81-87 (2003).

SUMMARY OF INVENTION

Technical Problem

Thus, there is a need for new safe and effective treatments for vasomotor symptoms. The present inventor discovered a new treatment for vasomotor symptoms by administering 4-({(4-cyclopropylisoquinolin-3-yl)[4-(trifluoromethoxy)benzyl]amino}sulfonyl)benzoic acid (hereinafter, referred to as "Compound A") at a lower dose, that is a transient receptor potential melastatin-8 (TRPM8) antagonist. It has been considered that Compound A or a pharmaceutically salt thereof shows a hypothermic action due to a TRPM8 blockade action, thereby has an effect of vasomotor symptoms, however, it was found unexpectedly that Compound A or a pharmaceutically salt thereof has a therapeutic or prophylatic effect on vasomotor symptoms in human beings even at lower dose being unable to exert a hypothermic action. Hence, Compound A or a pharmaceutically salt thereof may be administered at an unexpected lower dose to a subject who is suffered from vasomotor symptoms so as to improve (that is, suppress) an occurrence frequency of vasomotor symptoms.

Transient receptor potential (TRP) channels are non-selective cation channels that are activated by a variety of physical (e.g., temperature, osmolarity, mechanical) and chemical stimuli. A subset of the TRP channel superfamily is thermoresponsive, each channel activated over a discrete temperature range, cumulatively spanning from noxious cold to noxious heat. TRPM8 belongs to the melastatin subgroup of the TRP channel superfamily. TRPM8 is sensitive to cold temperature and menthol, and thus is also called the cold and menthol receptor-1 (CMR-1). McKemy et al., "Identification of a cold receptor reveals a general role for TRP channels in thermosensation," Nature, Vol. 416, No. 6876, pp. 52-58 (2002). TRPM8 is known to be stimulated by cool to cold temperatures (8 to 28° C.) as well as by chemical substances such as menthol and Icilin.

TRPM8 is located on primary nociceptive neurons (A-δ and C-fibers) and is also modulated by inflammation-mediated second messenger signals. Abe et al., "Ca2±-dependent PKC activation mediates menthol-induced desensitization of transient receptor potential M8," Neuroscience Letters, Vol. 397, No. 1-2, p. 140-144 (2006); Premkumar et al., "Down-regulation of Transient Receptor Potential Melastatin 8 by Protein Kinase C-Mediated Dephosphorylation," The Journal of Neuroscience, Vol. 25, No. 49, p. 11322-11329 (2005). TRPM8 is highly expressed in sensory neurons of the trigeminal and dorsal root ganglia. TRPM8 is also known to be expressed in the brain, lung, bladder, gastrointestinal tract, blood vessels, prostate, and immune cells.

TRPM8 antagonists and their use in treatments have been disclosed in previous patent filings (see, e.g., U.S. Pat. Nos. 8,987,445; 9,096,527; International Patent Publication No. WO 2014/042238). These disclosures report uses such as for the treatment of chronic pain (e.g., neuropathic pain), urologic disease, gastrointestinal disease, and cephalalgia. None of these disclosures, however, describe treating or preventing vasomotor symptoms with a TRPM8 antagonist.

Solution to Problem

The present disclosure is directed to a method for treating or preventing vasomotor symptoms in a subject in need thereof, comprising administering to the subject a lower dose of Compound A or a pharmaceutically acceptable salt thereof.

The present disclosure is also directed to a composition comprising a lower dose of Compound A or a pharmaceutically acceptable salt thereof for treating or preventing vasomotor symptoms in a subject and a pharmaceutically acceptable carrier.

The accompanying drawings are incorporated in and constitute a part of this specification.

BRIEF DESCRIPTION OF DRAWINGS

FIG. 1 shows the study design of a planned Phase I, randomized, double-blind, placebo-controlled study to assess the safety, tolerability and pharmacokinetics of multiple doses of Compound A as described herein in female subjects experiencing vasomotor symptoms.

FIG. 2 shows a change in Mean observed value in Vasomotor Symptoms (VMS) frequency over time within 24-hour after the first dose during the 14 days of treatment period. In the FIG. 2, each of the triangle or square symbol shows the result for 5 mg of Compound A or Placebo, respectively.

FIG. 5 shows a Study design for a randomized, double-blind, placebo-controlled study to assess the effect of 4-({(1-cyclopropylisoquinolin-3-yl)[4-(trifluoromethoxy)benzyl]amino}sulfonyl)benzoic acid or a pharmaceutically acceptable salt thereof on the frequency and severity of vasomotor symptoms in postmenopausal women.

FIG. 6 shows a change in core body temperature over time within 24 hour pre-dose and post dose on Visit 1, 7, 10 and 14 in 5 mg administered group. In this FIG. 6, filled circle symbol shows the results for all dosing groups of compound A combined into one single curve on baseline day (Visit day-1), and each of open diamond shape, open square, open circle and cross symbol shows the results for 5 mg of compound A on Visit day 1, 7, 10 and 14, respectively.

FIG. 7 shows pharmacometrics fructification in virtual clinical trials, and specifically, the simulated pharmacological effects on multiple dose of 5, 10, 20 and 50 mg of Compound A at Day 1 and Day 14. In this FIG. 7, upper, middle and lower panels show the changes in Mean simulated value of core body temperature, skin blood flow rate, as a measurable value related with efficiency of heat transfer from core body, and Vasomotor Symptoms (VMS) frequency over time within 24-hour, respectively.

FIG. 8 shows a pictorial representation of a model of heat flow in a human subject.

DESCRIPTION OF EMBODIMENTS

Description

Figure 3A:
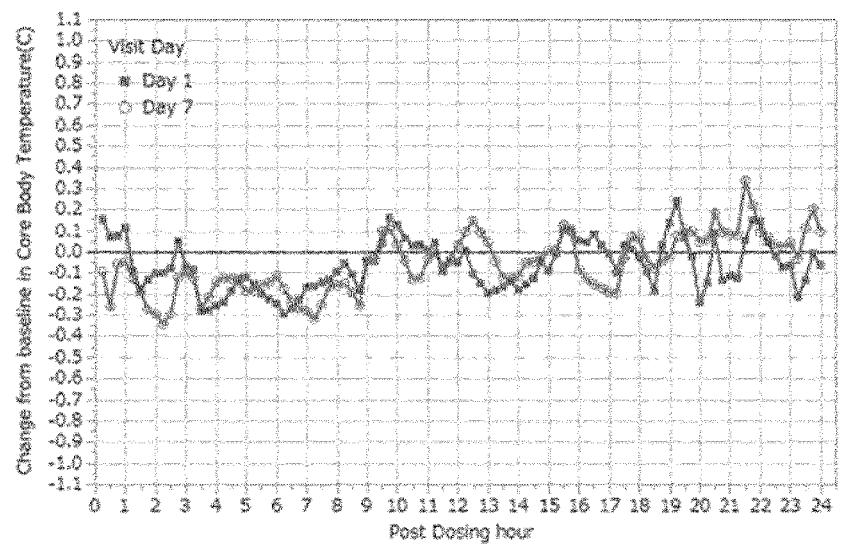
FIG. 3 shows a change from baseline in core body temperature over time within 24 hour post-dose on the Visit Day 1 or 7 in placebo (FIG. 3A) or 5 mg administered group (FIG. 3B). In each of the FIG. 3, each of square or open circle symbol shows the results for 5 mg of Compound A or Placebo on the Visit Day 1 or 7, respectively.

It is to be understood that both the foregoing general description and the following detailed description are exemplary and explanatory only and are not restrictive of the invention, as claimed. It should also be understood that the present disclosure is not limited to specific active agents, formulations, dosing regimens, and the like, as such may vary.

Particular aspects of the disclosure are described in greater detail below. The terms and definitions as used in the present application and as clarified herein are intended to represent the meaning within the present disclosure.

The term of "lower dose" as used herein may be a dose of Compound A or a pharmaceutically acceptable salt thereof as long at the dose, an occurrence frequency of vasomotor symptoms may be improved (that is, suppressed) while a hypothermic action being not shown when Compound A or a pharmaceutically acceptable salt thereof is administered. Typical examples of a daily dose thereof include 10 mg or less, preferably the range of 1 mg to 10 mg, and more preferably the range of 1 mg to 5 mg or 5 mg to 10 mg.

The daily dose of Compound A or a pharmaceutically acceptable salt thereof may be any dose being 10 mg or less, and specifically includes 10 mg, 9.5 mg, 9 mg, 8.5 mg, 8 mg, 7.5 mg, 7 mg, 6.5 mg, 6 mg, 5.5 mg, 5 mg, 4.5 mg, 4 mg, 3.5 mg, 3 mg, 2.5 mg, 2 mg, 1.5 mg, 1 mg, 0.5 mg, 0.25 mg, 0.1 mg, or 0.05 mg. A preferred example of the daily dose thereof includes 10 mg, 9.5 mg, 9 mg, 8.5 mg, 8 mg, 7.5 mg, 7 mg, 6.5 mg, 6 mg, 5.5 mg, 5 mg, 4.5 mg, 4 mg, 3.5 mg, 3 mg, 2.5 mg, 2 mg, 1.5 mg, or 1 mg. Also, a preferred example of the daily dose thereof includes 10 mg, 9.5 mg, 9 mg, 8.5 mg, 8 mg, 7.5 mg, 7 mg, 6.5 mg, 6 mg, 5.5 mg, or 5 mg. Further, a preferred example of the daily dose thereof includes 5 mg, 4.5 mg, 4 mg, 3.5 mg, 3 mg, 2.5 mg, 2 mg, 1.5 mg, or 1 mg. Among them, the daily dose is preferably 10 mg, 5 mg or 1 mg, and the daily dose of 5 mg is particularly preferred.

As used herein, the singular forms "a," "an," and "the" include plural reference unless the context dictates otherwise.

The terms of "approximately" and "about" mean to be nearly the same as a referenced number or value, including an acceptable degree of error for the quantity measured given the nature or precision of the measurements. As used herein, the terms "approximately" and "about" should be generally understood to encompass ±20% of a specified amount, frequency or value. Numerical quantities given herein are approximate unless stated otherwise, meaning that term "about" or "approximately" can be inferred when not expressly stated. "Vasomotor symptoms," as used herein, are known in the art and include all hot flashes, whether mild, moderate, or severe. Vasomotor symptoms may also include, but are limited to, night sweats and flushes.

The term of "hot flashes" as used herein refers to episodic sensations of heat, optionally accompanied by flushing and sweating, also optionally accompanied by tachycardia and chills. "Hot flash" as used herein may refer to hot flashes associated with menopause, with the symptoms or effects of a medical condition, with the side effects of a treatment for a medical condition, e.g., as a side effect of cancer treatment, or with any other triggers or causes of hot flashes. The term also includes "hot flushes." "Night sweats" are hot flashes that occur during sleep.

The term of "treating" or "preventing" vasomotor symptoms or the "treatment" or "prevention" of vasomotor symptoms as used herein includes one or more of (1) reducing, minimizing, or eliminating the occurrence or frequency of vasomotor symptoms; (2) relieving vasomotor symptoms when they occur; (3) reducing or minimizing the severity of (or palliating) or eliminating one or more symptoms of vasomotor symptoms; and (4) delaying the progression or development of vasomotor symptoms. The compositions and methods described herein may treat or prevent vasomotor symptoms (e.g., hot flashes) that occur at night (i.e., night sweats). In these embodiments, treating or preventing as described herein may also include reducing time to initial onset of sleep, increasing total sleep time, reducing the number of sleep disturbances or awakenings, and increasing the deeper levels of sleep.

As used herein, the term of a "subject" may be a human or an animal.

As used herein, the term of "core body temperature" refers to the internal body temperature of a subject. Core body temperature can be measured using techniques known in the art. In some embodiments, invasive means are used, such as placing a temperature probe into the oesophagus, pulmonary artery, or urinary bladder. In some embodiments, core body temperature is measured at a digestive organ. In some embodiments, core body temperature is measured at noninvasive sites, such as the rectum, oral cavity, axilla, temporal artery, or external auditory canal. In some embodiments, core body temperature is consistently measured at the same site, e.g., when evaluating the occurrence and/or extent of a decrease in core body temperature of a subject.

The term of "administer," "administration," or "administering" means the step of providing, giving, dosing and/or prescribing a drug according to the disclosure to an individual, or the step of an individual receiving, applying, taking, and/or consuming a drug according to the disclosure. The route of administration of an active agent or composition according to the present disclosure may be by any route of administration, for example, oral, parenteral, transmucosal, intranasal, inhalation, or transdermal.

The term of "perimenopausal woman" refers to a woman within the interval in which the woman's body makes a shift from more-or-less regular cycles of ovulation and menstruation toward permanent infertility or menopause. The interval may be a period of a few months, to several years, to 15 years or more before menopause. "Perimenopause" is also known as the menopausal transition. A "postmenopausal woman" refers to a woman who has undergone menopause, i.e., experienced twelve consecutive months without menstruation. A "menopausal woman" as used herein includes both a perimenopausal woman and a postmenopausal woman as defined herein. The menopause in these women may be either natural (such as with age), surgical (such as by removal of both ovaries), or induced by chemical treatment (such as by treatment with estrogen antagonists, e.g. fulvestrant, raloxifene, tamoxifen, or toremifene).

The present inventor discovered a new treatment for vasomotor symptoms by administering Compound A, which is a TRPM8 antagonist, at a lower dose. Without wishing to be bound by any particular theory, the present inventor considers that one of the reason why Compound A has a treatment or prevention effect on vasomotor symptoms at lower dose being unable to exert a hypothermic action may be due to the following possible theory.

The reduction in vasomotor symptoms that has been proven to occur in the context of TRPM8 receptor blockade is dependent on a series of causal interactions of biological systems. The effect of TRPM8 blockade on these systems is scalable.

Prospective and deliberate modification of the incremental of blockade of the TRPM8 receptor can be achieved via static, varying, and dynamic application of dosing, resulting in various methods by which magnitude, timing, and delivery of the TRPM8 blocking molecule to its target can be modified in experimental and clinical use. Pulsatile, intermittent, adjustable, and continuous approaches to dosing, for example, but not limited to these examples, via any of several dosing routes, including oral, rectal, vaginal, intravenous, intrathecal, intranasal, buccal, inhalation, topical, and various methods of injection into the body, for example, but not limited to these example, will create will a variety of physiologic responses by which various aspects of the sensory system, cardiovascular system, respiratory system, gastrointestinal system, reproductive system, integumentary system, peripheral and central neu-rological system, thermoregulatory system, circadian regulatory system, sympathetic and parasympathetic systems, endocrine system, renal and urinary system, for example, and not limited to these examples, may be employed to reduce, ameliorate, interrupt, discontinue, or prevent the various manifestations of vasomotor symptoms.

TRPM8 related modifications of temperature sensation signaling from the peripheral skin to the hypothalamus, and influences on the resulting cascade of temperature effector mechanisms will produce scientifically and medically demonstrable changes to the course, timing, severity, frequency, relevance, and medical importance of vasomotor symptoms in individuals and study populations who, respectively, suffer from these symptoms.

Relevant physiologic characteristics include, but are not limited to, the core and peripheral body temperature, the amplitude, frequency, and regularity of circadian rhythm, all manifestations of the TRPM8 receptor, all manifestations of interaction and blockade of the TRPM8 receptor, all aspects of the integrity of TRPM8 signaling, and all aspects of thermoregulation.

The effect of TRPM8 inhibition or blockade is ultimately manifested through the ability to control various physiological systems in order to better facilitate heat transfer through multiple compartments, with effects on heat within those predicted by the laws of thermodynamics.

Doses of scalable and potentially dynamically administered amounts of a TRPM8 inhibitor or blocker, delivered by any of several routes, allows core and peripheral temperature to be maintained or controlled acutely, and over time, in order that the circadian temperature curve can be continuously and dynamically modified. This process of acute, continuous, and dynamically modifiable temperature is dependent of the ability of the thermoregulatory system to variously sense modifications in the intensity, duration, and temporality of TRPM8 signaling. In the average patients with vasomotor symptoms, there is the descriptive flattening of the normal and expected circadian temperature rhythm and cycle. Specifically, the range of normal diurnal temperature change is narrowed.

As illustrated in FIG. 8, four thermal compartments are of primary importance. 1. There is an energy and heat generating compartment. 2. There is a core body (head, thorax, and abdomen) compartment. 3. There is a peripheral skin compartment.4. There is an external environmental compartment.

An integrated model of human thermoregulation (hTR) can be understood from elements described in a heat transfer model of human body (modified Gagge's Two-node model, ASHRAE Transactions, 77: 247-62. (1971); Metabolic heat production model with circadian rhythm, J. Pharmacol. Exp. Ther., 317: 209-19. (2006)) in the context of physiology outlined in a neuronal thermoregulation model(Temperature, 1: 142-9. (2014)).

In healthy normal function, a heat cycle exists by which heat moves sequentially through these compartments, and by which heat accrues and dissipates in a 24 hour rhythm. Heat is normally dissipated from the central compartment to the peripheral skin, and then to the environment, with a typical evening into night drop in core temperature, followed by accrual and warming before waking. When this normal cycle is disturbed, and heat cannot be efficiently moved to the peripheral skin and dissipated to the external compartment, temperature rises, and non-preferred paths for heat dissipation are recruited. When the face, head, chest, and other areas are recruited acutely, blood is shifted to the surface of these areas, and heat is dissipated to the external compartment in an urgent and in an inefficient manner via surface vasodilatation and resulting sweating. This process is subjectively recognized as a "hot flash", and is the equivalent of an "emergency relief valve" for accrued body heat. The heat that is dissipated in the burst of a "hot flash" is insufficient to restore the normal physiologic circadian temperature curve, but does allow for return to a functional homeostasis. It is a "short term" fix.

Blockade of TRPM8 can be scaled therapeutically to restore homeostasis. Heat production is reduced, which is associated with a greatly lessened need for inefficient heat release via a "hot flash", hence, a pharmacologic homeostasis. Blockade can also be scaled to restore a more normally physiologic temperature curve that may be predicted to produce additional cardiovascular and sleep benefits.

Applying engineering principles of amplitude, frequency, pulsation, impulse, damping, and power, the temperature curve can be influenced in a variety of ways. In practical manifestation, small blockade of TRPM8 signaling (low dose), is just enough to allow the adjustment of the thermoregulatory system to compensate without the need to employ hot flashes for homeostasis. Hence, in this case (low dose) there is no measureable change in core temperature. At some doses of Compound A (approximately 5-10 mg/day prior to time of sleep), the introduction of the drug, when specifically timed to take effect during the expected "cooling" leg of the temperature cycle, appears to re-establish a more normal circadian rhythm, re-establishing the normal circadian temperature cycle that is most typically lost (flattened) in patients suffering from vasomotor symptoms (J Steroid Biochem Mol Biol. 2014 July; 142: 115-120).

This re-establishment of a virtuous and efficient temperature rhythm and heat flow process can be visualized as a pharmacologically established temperature dip below the pre-treatment "flattened" temperature curve, followed by a more normal peak above the pre-treatment flattened curve, thus approximating the healthy circadian state.

With the re-establishment of the curve, heat is better transferred from the core to the environment, preventing the need for "hot flashes" to "off load" heat urgently.

Hot flashes, for many individuals, are most bothersome at the time of sleep onset, and the first hours of sleep, when interactions with the brain normally instruct the body to cool, but as normal passive and active cooling fails, and perhaps, the heat engine fails to slow heat production. This apparent mismatch between circadian drive to cool, and the inability of the body to cool sufficiently, may be manifested in hot flashes.

Compound A works in concert with normal circadian drive, through timed administration matched to the circadian curve, and the specific intent to modify the curve, to facilitate a reduction in body temperature, or, specifically and alternatively, to facilitate passive and active body cooling, and/or reduction of energetic output of the heat engine, via interruption of the TRPM8 cool temperature sensor.

Because the effective pharmacodynamic blockade of the receptor is may be deliberately temporally modified (i.e. short versus long), the dose of Compound A can be deliberately pulsed as a single nightly dose to drive a pharmacological normalization of the temperature curve, first through cooling, and then, with metabolism leading to its elimination, a subsequent physiologic warming prior to the expected morning time of waking. Intensity of the pulse deliberately includes concepts of magnitude, amplitude, duration, and intensity that may be modified with various pharmacokinetic and pharmacodynamic scaling. Further, concepts of wave mechanics, by which a rhythm (specifically, human circadian rhythm) may be modified or modulated, are inherent and central to the mechanism by which Compound A creates beneficial clinical effect.

It necessarily follows that the intensity, frequency, number, magnitude, and clinical interference of vasomotor symptoms are reduced by the therapeutic mechanism of Compound A. Additionally associated with these effects, the sleep pattern is normalized and sleep efficiency is improved in those with evidence of impaired sleep in the context of vasomotor symptoms and burden. In total, these effects support a dose in the 10 mg or less, particularly 1 to 10 mg range, administered nightly prior to bedtime, as effective, as hot flashes are reduced, circadian rhythm is restored, and sleep is normalized. While, Larger doses of Compound A may allow for an extended time of cooling, and more temporally prolonged, reductions in core temperature, facilitating the amelioration of vasomotor symptoms including hot flashes, ultimately leading to clinically relevant improvements in quality of life, pulse characteristics, and timing of administration of certain and sufficient lower doses on Compound A have been shown to have unique effects to restore a more natural 24 hour circadian resonance curve and frequency, with associated thermodynamic efficiencies.

These relationships can be mathematically expressed and modelled based on human clinical data collected during previous studies of Compound A.

These relationships can be further mathematically described by the equations whose elements are tabulated herein (see Table 1), and which model for the effect of lower doses of Compound A to exert its primary effect through a reduction in metabolic heat production of approximately 50%, leading to a diminution of the number, frequency, and intensity of vasomotor symptoms.

TABLE 1

| Parameters | Values | Descriptions |
|---|---|---|
| Ht | Individual | Height [cm] |
| Wt | Individual | Weight [kg] |
| $W_{core}$ | 0.95 · Wt | Weight of core body [kg] |
| $W_{skin}$ | 0.05 · Wt | Weight of skin [kg] |
| S | $\sqrt{Ht \cdot Wt/3600}$ | Body surface area [m$^2$] |
| $c_{core}$ | 0.97 | Specific heat in core body [Wh/kgK] |
| $c_{skin}$ | 0.97 | Specific heat in skin [Wh/kgK] |

TABLE 1-continued

| Parameters | Values | Descriptions |
|---|---|---|
| $T_a$ | 28 | Temperature of ambient air [degree C.] |
| $\varphi_a$ | 0.5 | Relative humidity (fraction) |
| $P_a$ | 28.62 | Saturated vapor pressure of ambient air [mmHg] |
| r | 0.7 | Evaporative heat of water [J/kg] |
| $\alpha_c$ | 3.1 | Convective heat transfer coefficient [W/m$^2$K] |
| $\alpha_r$ | 4.65 | Radiative heat transfer coefficient [W/m$^2$K] |
| $\alpha'$ | 14.61 | moisture transfer coefficient [kg/m$^2$s mmHg] |
| $\theta$ | 0 | Working efficiency (fraction) |
| $K_{min}$ | 5.28 | Minimum heat conductance by skin tissue [W/m$^2$K] |
| $c_{bl}$ | 1.163 | Specific heat in blood [Wh/kgK] |
| $T_{core, set}$ | 36.6 | Setting point of core temperature [degree C.] |
| $T_{skin, set}$ | 34.1 | Setting point of skin temperature [degree C.] |
| $k_{sw}$ | 100 | Coefficient of sweating rate [kg/m$^2$ h degree C.$^2$] |
| $k_{basal}$ | 6.3 | Skin blood flow rate under thermally neutral conditions [L/m$^2$ h] |
| $k_{dil}$ | 75 | Coefficient of vasodilation [L/m$^2$ h] |
| $k_{con}$ | 0.5 | Coefficient of vasoconstriction [1/degree C.] |

Thus, a thermodynamic model of heat transfer, as modified by Compound A, at lower doses, follows, and employs differential equations based on the first law of thermodynamics.

$$\frac{dT_{core}}{dt} = (q_{met} - q_{res} - q_{bl} - q_{cond}) \cdot \frac{S}{c_{core} \cdot W_{core}}$$

$$\frac{dT_{skin}}{dt} = (q_{bl} + q_{cond} - q_{conv} - q_{radi} - q_{diff} - q_{rsw}) \cdot \frac{S}{c_{skin} \cdot W_{skin}}$$

Rate equations of heat production, transfer, and loss in the model are further described:

$$q_{met} = (1-\theta) \cdot M$$

$$q_{res} = 0.0023 \cdot M \cdot (44 - \varphi_a \cdot P_a)$$

$$q_{bl} = c_{bl} \cdot v_{bl} \cdot (T_{core} - T_{skin})$$

$$q_{cond} = K_{min} \cdot (T_{core} - T_{skin})$$

$$q_{conv} = \alpha_c \cdot F_{cl} \cdot (T_{skin} - T_a)$$

$$q_{radi} = \alpha_r \cdot F_{cl} \cdot (T_{skin} - T_a)$$

$$q_{diff} = P_{wet} \cdot r \cdot \alpha' \cdot (P_{skin} - \varphi_a \cdot P_a) - q_{rsw}$$

$$q_{rsw} = r \cdot m_{sw} \cdot 2^{(T_{skin} - T_{skin,set})/3}$$

An equation of the regulatory sweating rate (regulated by autonomic system) is further described:

$$m\_sw = k\_sw \cdot (T\_core - T\_(core, set)) \cdot (T\_skin - T\_(skin, set)) \cdot 1/(3600 \cdot 1000)$$

An equation of the blood flow rate (regulated by autonomic system) is also described:

$$v\_bl(k\_basal + k\_dil \cdot (T\_core - T\_(core,))/(1 + k\_con \cdot (T\_(skin,set) - T\_skin)) \cdot 1/3600$$

These effects are then described within the context of a circadian model:

$$M_c = \begin{cases} M_{day} & \text{for } t \in \{[0, t_{night}], [t_{day}, t_{night} + 24], \ldots\} \\ M_{night} & \text{for } t \in \{[t_{night}, t_{day}], [t_{night} + 24, t_{day} + 24], \ldots\} \end{cases}$$

$$\frac{dM}{dt} = -k_m \cdot (M - M_c)$$

In summary, this model provides support for an effect of Compound A to provide a beneficial effect on reducing vasomotor symptoms that is based on sensory integration and homeostatic reduction in thermal heat generation, rather than a primary effect to reduce core body temperature. The model supports a predicted optimal human clinical effect at a dose of 10 mg or less per day (see FIG. 7).

The present disclosure is directed to a method for treating or preventing vasomotor symptoms in a subject in need thereof, comprising administering to the subject a lower dose of Compound A or a pharmaceutically acceptable salt thereof. In some embodiments, the vasomotor symptom is hot flashes. In some embodiments, the subject is a human. The subject may be male or female. It is envisioned that the methods will be used for subjects that are prone to having, are having, or are expected to have vasomotor symptoms, such as hot flashes. The subject in need thereof may suffer from or anticipate suffering from vasomotor symptoms associated with menopause, with the symptoms or effects of a medical condition, with the side effects of a treatment for a medical condition, or with any other trigger or cause of vasomotor symptoms.

Subjects include, but are not limited to, menopausal women, subjects who are taking or anticipate taking antiestrogen drugs (such as tamoxifen or aromatase inhibitors), subjects who are anticipating or have gone through surgery, or subjects having or anticipating having any other condition or undergoing or anticipating undergoing any other treatment that results in changes in hormone levels.

Subjects further include, but are not limited to, oncology patients. For example, subjects may include those who are anticipating, are undergoing, or have undergone cancer treatment, such as through surgery or radiation therapy. For example, subjects may include those who are anticipating, are undergoing, or have undergone gonadal ablative therapy or gonadal hormonal suppressive therapy. Where the subject is undergoing or has undergone cancer treatment, the cancer treatment can be a treatment which affects the hormone levels of the subject, for example, hormonal therapy treatment for breast cancer, ovarian cancer and prostate cancer. Examples of hormonal therapies for cancers include: selective estrogen receptor antagonists including tamoxifen (Nolvadex (registered trademark)), raloxifene (Evista (registered trademark)), lasofoxifene (Fablyn) and toremifene (Fareston (registered trademark)); antiestrogen drugs including fulvestrant (Faslodex (registered trademark)); aromatase inhibitors including anastrozole (Arimidex (registered trademark)), letrozole (Femara (registered trademark)), vorozole (Rivizor), formestane (Lentaron), fadrozole (Afema) and exemestane (Aromasin (registered trademark)); luteinizing-hormone-releasing hormone (LHRH) agonists including goserelin (Zoladex (registered trademark)), leuprolide (Lupron (registered trademark)); luteinising hormone (LH) blockers including buserelin, leuprorelin (Prostap (registered trademark)), histrelin (Vantas (registered trademark)), deslorelin (Suprelorin (registered trademark)), nafarelin (Synarel (registered trademark)) and triptorelin (Decapeptyl (registered trademark)); anti androgens including flutamide (Drogenil (registered trademark)), nilutamide (Nilandron (USA)/Anandron (Canada)) and bicalutamide (Casodex (registered trademark)); gonadotrophin releasing hormone (GnRH) blocker including degarelix (Firmagon (registered trademark)); and abiraterone (Zytiga (registered trademark)).

Subjects also include, but are not limited to, subjects who are anticipating or have gone through surgically-induced hormonal variations, such as hysterectomy, oophorectomy, and orchiectomy.

The lower dose of Compound A or a pharmaceutically acceptable salt thereof may be administered as a composition comprising the lower dose of Compound A and a pharmaceutically acceptable carrier. In certain embodiments, the composition is a pharmaceutical composition.

Administration of a lower dose of Compound A or a pharmaceutically acceptable salt thereof or composition thereof may be on an as-needed basis or may be on a schedule, such as in an ongoing dosing regimen. For example, the necessary amount of Compound A or a pharmaceutically acceptable salt thereof or the composition thereof may be administered as needed, such as immediately upon sensing the onset of vasomotor symptoms, such as a hot flash. Scheduled administration may be on a uniform schedule or on a non-uniform schedule where the frequency of administration is correlated with the circadian rhythm of vasomotor symptoms, either in the symptomatic population or of the individual treated. Even if scheduled administration is used, it is possible to administer the compound on an as-needed basis if vasomotor symptoms are still experienced. In some embodiments, the lower dose of Compound A or a pharmaceutically acceptable salt thereof or composition thereof is administered daily, such as once daily or twice daily. In some embodiments, the timing and frequency of administration is chosen to target the treatment or prevention of vasomotor symptoms (e.g., hot flashes) that occur at night (i.e., night sweats) as described herein. In certain embodiments, the lower dose of Compound A or a pharmaceutically acceptable salt thereof or composition thereof is administered in the evening, such as a dosing regimen comprising once daily administration in the evenings. In some embodiments, the lower dose of Compound A or a pharmaceutically acceptable salt thereof or composition thereof is administered before bedtime, such as a dosing regimen comprising once daily administration before bedtime.

The administration of Compound A or a pharmaceutically acceptable salt thereof or composition thereof is not limited to any particular route of administration, such as oral administration.

A combination therapy wherein Compound A or a pharmaceutically acceptable salt thereof is administered with one or more additional active agents is also within the scope of the present disclosure. Such combination therapy may be carried out by administration of the different active agents in a single composition, by concurrent administration of the different active agents in different compositions, or by sequential administration of the different active agents. Derivatives and analogs of the active agents and classes of active agents disclosed herein that induce the desired effect are within the scope of the present disclosure. Here, the term of "active agent" refers to a chemical compound that induces a desired effect.

Examples of additional active agents include, but are not limited to, active agents for treating or preventing vasomotor symptoms or active agents useful for treatment of other signs and symptoms of hormonal variation, such as estrogen, estrogen receptor modulator, estrogen agonist, androgen receptor modulator, peptide hormone, neurokinin class agents (neurokinin-3 receptor antagonist, etc.), sedative, hypnotic, anxiolytic, antipsychotic, antianxiety agent, minor tranquilizers, benzodiazepine, barbiturate, serotonin (5-HT) agonist, selective serotonin reuptake inhibitor (SSRI's), 5HT-2 antagonist, non-steroidal anti-inflammatory drug, oral contraceptive, progesterone, progestin, monoamine oxidase inhibitor, carbohydrate mixture and the like, or physical method such as a cooling agent. Further examples of additional active agents include, but are not limited to, estrogen, progesterone, clonidine, venlafaxine, megestrol acetate, mirtazapine, a nonsteroidal anti-inflammatory, such as acetaminophen, alprostadil, aspirin, diclofenac, etodolac, ibuprofen, indomethacin, ketoprofen, ketorolac tromethamine, misoprostol, nabumetone, naproxen, naproxen sodium, oxaprozin, piroxicam, spironolactone, spironolactone with hydrochlorothiazide, or trovafloxacin; a corticosteroid; a selective cyclooxygenase-2 inhibitor, such as celecoxib, etoricoxib, parecoxib, rofecoxib, valdecoxib, meloxicam, flosulide, nimesulide, MK-663, NS 398, DuP 697, SC-58125, SC-58635, or RS 57067, adinazolam, abiraterone, allobarbital, alonimid, alprazolam, amitriptyline, amobarbital, amoxapine, anastrozole, bentrazepam, benzoctamine, bicalutamide, brotizolam, bupropion, buserelin, buspirone, butabarbital, butalbital, capuride, carbocloral, chloral betaine, chloral hydrate, chlordiazepoxide, clometherone, clomipramine, cloperidone, clorazepate, clorethate, clozapine, cyprazepam, degarelix, delmadinone, desipramine, deslorelin, dexclamol, diazepam, dichloralphenazone, divalproex, diphenhydramine, doxepin, droloxifene, estazolam, estradiol, estrogen, ethchlorvynol, etomidate, exemestane, fadrozole, fenobam, flunitrazepam, flurazepam, flutamide, fluvoxamine, fluoxetine, formestane, fosazepam, fulvestrant, glutethimide, goserelin, halazepam, histrelin, hydroxyzine, idoxifene, imipramine, lasofoxifene, leuprolide, lithium, letrozol, leucine, leuprolide, leuprorelin, lorazepam, lormetazepam, maprotiline, mecloqualone, melatonin, mephobarbital, meprobamate, methaqualone, midaflur, midazolam, nafarelin, nafoxidine, nefazodone, nitromifene, nilutamide, nisobamate, nitrazepam, nociceptin, nortriptyline, ormeloxifene, oxazepam, paraldehyde, paroxetine, pentobarbital, perlapine, perphenazine, phenelzine, phenobarbital, prazepam, progesterone, promethazine, propofol, protriptyline, quazepam, raloxifene, reclazepam, roletamide, secobarbital, sertraline, suproclone, tamoxifene, temazepam, thioridazine, toremifene, tracazolate, tranylcypromaine, trazodone, trioxifene, triazolam, triptorelin, trepipam, tricetamide, triclofos, trifluoperazine, trimetozine, trimipramine, uldazepam, valproate, venlafaxine, vorozole, zaleplon, zolazepam, zolpidem, and salts thereof, and combinations thereof, and the like, as well as admixtures and combinations thereof. Further examples of additional active agents include, but are not limited to, selective estrogen receptor antagonists including tamoxifen (Nolvadex (registered trademark)), raloxifene (Evista (registered trademark)), and toremifene (Fareston (registered trademark)); antiestrogen drugs including fulvestrant (Faslodex (registered trademark)); aromatase inhibitors including anastrozole (Arimidex (registered trademark)), letrozole (Femara (registered trademark)) and exemestane (Aromasin (registered trademark)); Luteinizing-hormone-releasing hormone (LHRH) agonists including goserelin (Zoladex (registered trademark)), leuprolide (Lupron (registered trademark)); Luteinizing hormone (LH) blockers including buserelin, leuprorelin (Prostap (registered trademark)), histrelin (Vantas (registered trademark)) and triptorelin (Decapeptyl (registered trademark)); anti androgens including flutamide (Drogenil (registered trademark)) and bicalutamide (Casodex (registered trademark)); Gonadotrophin releasing hormone (GnRH) blocker including degarelix (Firmagon (registered trademark)); and abiraterone (Zytiga (registered trademark)).

In some embodiments, the present disclosure includes a composition comprising a lower dose of Compound A or a pharmaceutically acceptable salt thereof for treating or preventing vasomotor symptoms and a pharmaceutically acceptable carrier. In certain embodiments, the composition is a pharmaceutical composition. The composition can be used with an inert carrier suitable for each administration method, and can be formulated into conventional preparations (e.g., tablets, granules, capsules, powder, solution, suspension, emulsion, injection, infusion, etc.). As such a carrier, there may be mentioned, for example, a binder (e.g., gum arabic, gelatin, sorbitol, polyvinylpyrrolidone, etc.), an excipient (e.g., lactose, sugar, corn starch, sorbitol, etc.), a lubricant (magnesium stearate, talc, polyethylene glycol, etc.), a disintegrator (e.g., potato starch, etc.) and the like, which are pharmaceutically acceptable. When the composition is used as an injection solution or an infusion solution, it can be formulated by using, e.g., distilled water for injection, physiological saline, an aqueous glucose solution, etc.

In certain embodiments, the present disclosure includes a use of a lower dose of Compound A or a pharmaceutically acceptable salt thereof or a composition comprising the same as an active ingredient for treating or preventing vasomotor symptoms in a subject in need thereof. Also in certain embodiments, the present disclosure includes a use of a lower dose of Compound A or a pharmaceutically acceptable salt thereof in a preparation of a medicament for treating or preventing vasomotor symptoms.

It is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLES

Example 1: Phase I, Randomized, Double-Blind, Placebo-Controlled Study to Assess the Safety, Tolerability and Pharmacokinetics of Multiple Doses of Compound A in Female Subjects Experiencing Vasomotor Symptoms Study Design: This was a Phase Ib, randomized, double blind, placebo controlled study. The study design is illustrated in FIG. 1. Following the initial Screening visit, eligible subjects was given an actigraphy event monitor (watch) to record episodes of flashing as Vasomotor symptoms (VMS) events during a period of 2 weeks during Screening, in order to confirm VMS eligibility criteria (≥7 VMS/day on average during 2 weeks). Subjects may be required to return to the site during the Screening period to read or exchange the actigraphy event monitor. Subjects deemed eligible following review of VMS data were invited to attend the Clinical research unit (CRU) for one residential period of 16 days duration, including 14 days of Investigational Medicinal Product (IMP) administration. Subjects were admitted to the CRU 1 day prior to dosing (Day-1). No medication was administered on Day-1. On Day 1, subjects who meet the study eligibility criteria were randomized to receive one dose level of either Compound A (6 subjects) or a matching placebo (2 subjects) in a double-blind manner.

Randomized treatment was administered once nightly, starting on Day 1, for a total duration of 14 days.

The anticipated dose levels of Compound A to be administered are 50 mg for Cohort 1, 20 mg for Cohort 2 and 5 mg for Cohort 3. Progression to the next dose level and selection of the dose to be administered in Cohort 2 and Cohort 3 is based on emerging safety and tolerability data and available core body temperature data from the preceding dose cohort. If the dose escalation stopping criteria are met, then the dose for the subsequent cohort is reduced. The lowest potential dose to be assessed is 5 mg and the maximum dose for the study does not exceed 50 mg. The three cohorts are dosed sequentially with a fourth additional cohort being dosed, if necessary, to investigate other dose levels.

Subjects is discharged from the CRU after all 24 hour post-dose procedures are completed in the evening on Day 15 or in the early morning on Day 16 if deemed more convenient by the subjects, and return for a follow up visit on Day 21. The overall duration of participation for each subject is a maximum of 63 days (from the initial Screening visit on Day-42 to follow-up on Day 21).

Endpoints:
Primary Assessments
Safety and tolerability: Vital signs, ECG parameters, Clinical laboratory assessments, Physical examination, Adverse events and Assessment of overall tolerability
Secondary Assessments
Pharmacokinetics assessments
Core body temperature assessment
Change from baseline in core body temperature.
Exploratory assessments
Frequency of VMS and sleep assessments.
Mood and subjective sleep quality Five (5) mg of Compound A was administered to the female subjects experiencing Vasomotor Symptoms (VMS), and as the above-mentioned assessments, a Frequency of VMS and a Core body temperature assessment were examined.

For the Frequency of VMS, a change in Mean observed value in Vasomotor Symptoms (VMS) frequency was observed over time within 24-hour after the first dose during the 14 days of treatment period. Here a moderate VMS and a severe VMS were counted as a VMS frequency. The mean observed value in VMS frequency on the each Visit Days are summarized in Table 2. Pattern changes of the core body temperature at 1, 7, 10 and 14 days after administration of 5 mg of Compound A were shown in FIG. 6.

TABLE 2

| VISIT Day | Mean Observed Value | |
|---|---|---|
| | Placebo | Compound A |
| Baseline | 14.8 | 14.5 |
| Day 1 | 13.5 | 9.7 |
| Day 2 | 11.3 | 7.2 |
| Day 3 | 9.2 | 6.3 |
| Day 4 | 9.3 | 5.3 |
| Day 5 | 9.0 | 8.0 |
| Day 6 | 8.3 | 6.3 |
| Day 7 | 9.8 | 4.7 |
| Day 8 | 7.8 | 3.7 |
| Day 9 | 7.3 | 4.5 |
| Day 10 | 8.3 | 3.2 |
| Day 11 | 8.7 | 3.7 |
| Day 12 | 6.5 | 3.2 |
| Day 13 | 7.0 | 3.2 |
| Day 14 | 8.3 | 4.8 |

Each of the Mean Observed Values in VMS frequency for Placebo and Compound A were plotted as shown in FIG. 2. In the FIG. 2, each of the triangle or square symbol shows the result for 5 mg of Compound A or Placebo, respectively. As shown in FIG. 2, Compound A reduced the frequency of VMS significantly and Compound A had an immediate effect because the reduction effect of VMS frequency was shown at during the first night of active drug therapy or later, namely, within a few days of administration, compared to estrogen or selective Serotonin Reuptake Inhibitor such as Paroxetine.

Figure 3B:
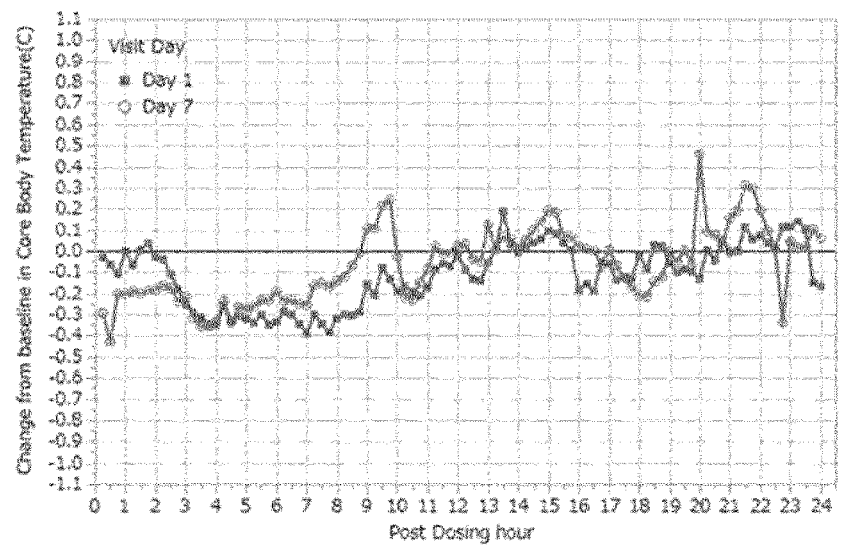
Figure 4A:
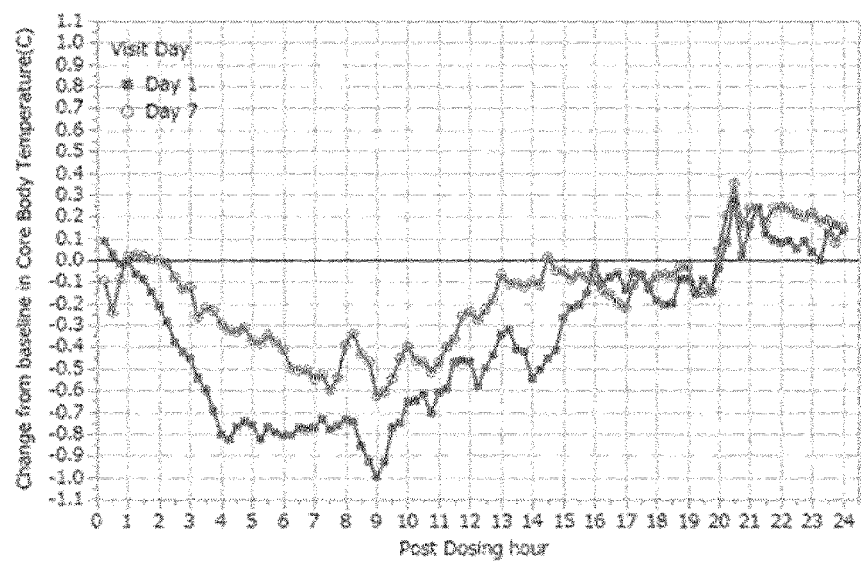
FIG. 4 shows a change from baseline in core body temperature over time within 24 hour post-dose on the Visit Day 1 or 7 in 20 mg (FIG. 4A) or 50 mg (FIG. 4B) administered group. In each of the FIG. 4, each of square or open circle symbol shows the results on the Visit Day 1 or 7, respectively.
Figure 4B:
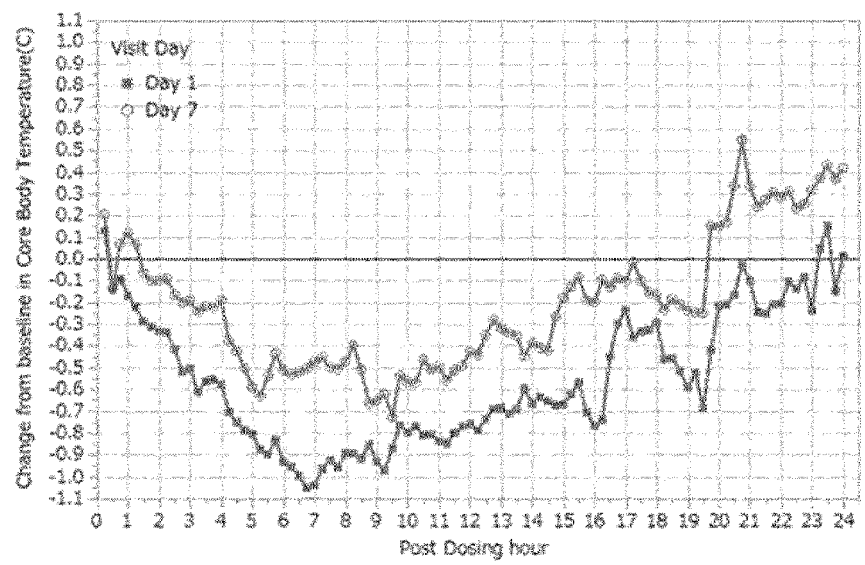

For the Core body temperature assessment, a change from baseline in core body temperature of the subjects was observed over time within 24 hours post-dose on the Visit 1 or 7. The test results of placebo (FIG. 3A) and 5 mg administered group (FIG. 3B) are shown in FIG. 3. The test results of 20 mg (FIG. 4A) and 50 mg (FIG. 4B) administered groups are shown in FIG. 4. Each of square or open circle symbol shows the results on the Visit Day 1 or 7, respectively. As shown in FIGS. 3 and 4, Compound A showed no significant reduced the core body temperature in 5 mg administered group like placebo, in comparison with each administered group given 20 mg and 50 mg, respectively.

Example 2: Phase II, A Randomized, Double-Blind, Placebo-Controlled Study to Assess the Effect of Compound A on the Frequency and Severity of Vasomotor Symptoms in Postmenopausal Women Subjects Experiencing Vasomotor Symptoms Study Design This was a Phase II randomized, double-blind, placebo-controlled study for dose selection.

Subjects meeting eligibility criteria were enrolled in a 2-week single blind Placebo Run-in period. All eligible subjects received single-blind placebo daily before bedtime. Following the Placebo Run-in period, subjects meeting eligibility criteria entered the 12-week, placebo controlled Double-blind Treatment period. The Double blind Treatment period had 4 arms including: placebo and Compound A 1, 5, and 10 mg. A single daily dose of study medication was administered before bedtime. An End of Study (EOS) Follow-up visit was conducted by phone for safety follow up 30 days after the end of the Double blind Treatment period. Total duration was 20 weeks, inclusive of the Screening and Follow up periods (see FIG. 5).

A planned interim assessment for safety, and a planned interim analysis for efficacy (futility) and safety was conducted during the study; enrollment proceeded without interruption.

Interim assessment for safety was conducted when approximately 25% of subjects had completed Week 12 in the Double-blind Treatment period.

Interim analysis for efficacy (futility) and safety was conducted when approximately 50% of subjects had completed Week 12 in the Double-blind Treatment period.

The primary endpoint was evaluated at Weeks 4 and 12.
Endpoints: Co-Primary Efficacy Endpoints
Change from baseline in the average daily frequency of moderate to severe VMS, defined as the sum of the number of moderate to severe VMS during 1 week divided by number of days with data. The daily score here and below were average scores from a 7-day period. Details were defined in the Statistical Analysis Plan (SAP).

Change from baseline in the average daily severity score of mild to severe VMS. Baseline VMS severity score was defined as $(2\times Fmo+3\times Fse)/(Fmo+Fse)$, and VMS severity score for a specific week during the double-blind treatment period was defined as $(1\times Fmi+2\times Fmo+3\times Fse)/(Fmi+Fmo+Fse)$, where Fmi, Fmo, and Fse are the daily frequencies of mild, moderate, and severe VMS, respectively, during each applicable study week.

Co-primary endpoints were evaluated at Week 4 and Week 12.

Secondary Efficacy Endpoints

Proportion of responders at Weeks 4 and 12 (i.e., subjects with cutoff number* or greater reduction in the average daily frequency of moderate and severe VMS compared to baseline)

Time to response, defined as time (in weeks) from randomization to the first time the subject meets responder criteria (i.e., cutoff number* or greater reduction from baseline in the average daily frequency of moderate and severe VMS)

Note: The cutoff number was calculated using anchor-based method. The cutoff number was defined as numerical value to maximize the sensitivity and the specificity, using Patient Global Impression of Change (PGIC) as the anchor.

Change from baseline to Weeks 4 and 12 in the Insomnia Severity Index (ISI) total score Other Efficacy Endpoints PGIC at Weeks 4 and 12

Change from baseline to Weeks 4 and 12 in the Pittsburgh Sleep Quality Index (PSQI)

Change from baseline to Weeks 4 and 12 in the Menopause-Specific Quality of Life (MENQOL)

Change from baseline to Weeks 4 and 12 in the 36-Item Short Form Health Survey (SF-36)

Change from baseline in the average daily severity score of moderate to severe VMS at Weeks 4 and 12, defined as $2\times Fmo+3\times Fse$ Pharmacokinetic (PK) Assessments Blood samples to assess plasma concentrations of Compound A were obtained at 5 visits during the Double-blind Treatment period.

Safety Assessments

Physical examination (including breast safety evaluation)

Vital signs (blood pressure, pulse and tympanic body temperature)

ECG parameters (including cardiac intervals: heart rate, PR, QRS, QT, QTcF and QTcB)

Clinical laboratory assessments (hematology, biochemistry, coagulation, and urinalysis)

Reproductive hormones (luteinizing hormone [LH], follicle stimulating hormone [FSH], and estradiol [E2])

Adverse events (AEs)

Endometrial safety (endometrial thickness, as measured by transvaginal ultrasound, and incidence of endometrial hyperplasia, as measured by endometrial biopsy)

Depression and anxiety as measured by 8-Item Patient Health Questionnaire (PHQ-8) and the 7-item Generalized Anxiety Disorder questionnaire (GAD7), respectively.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for treating vasomotor symptoms in a subject in need thereof, the method comprising:
administering to the subject 4-({(4-cyclopropylisoquinolin-3-yl)[4-(trifluoromethoxy)benzyl]amino}sulfonyl)benzoic acid or a pharmaceutically acceptable salt thereof at a daily dose ranging from 1 mg to 10 mg, wherein the vasomotor symptoms are hot flashes or night sweats.

2. The method according to claim 1, wherein the daily dose ranges from 5 mg to 10 mg.

3. The method according to claim 1, wherein the daily dose ranges from 1 mg to 5 mg.

4. The method according to claim 2, wherein the daily dose is 10 mg.

5. The method according to claim 3, wherein the daily dose is 5 mg.

6. The method according to claim 3, wherein the daily dose is 1 mg.

7. The method according to claim 1, wherein the subject is a human subject.

8. The method according to claim 7, wherein the human subject is a menopausal woman.

9. The method according to claim 7, wherein the human subject is a perimenopausal woman.

10. The method according to claim 7, wherein the human subject is a postmenopausal woman.

11. The method according to claim 7, wherein the human subject is a cancer patient.

12. The method according to claim 7, wherein the human subject is undergoing or has undergone a treatment for cancer.

13. The method according to claim 12, wherein the treatment for cancer is gonadal ablative therapy or gonadal hormonal suppressive therapies.

14. The method according to claim 7, wherein the human subject has undergone a surgery.

15. The method according to claim 14, wherein the surgery is a hysterectomy, oophorectomy, or orchiectomy.

16. The method according to claim 1, wherein the 4-({(4-cyclopropylisoquinolin-3-yl)[4-(trifluoromethoxy)benzyl]amino}sulfonyl)benzoic acid or pharmaceutically acceptable salt thereof is administered with onset of the vasomotor symptom.

17. The method according to claim 1, wherein the 4-({(4-cyclopropylisoquinolin-3-yl)[4-(trifluoromethoxy)benzyl]amino}sulfonyl)benzoic acid or pharmaceutically acceptable salt thereof is administered daily.

18. The method according to claim 17, wherein the 4-({(4-cyclopropylisoquinolin-3-yl)[4-(trifluoromethoxy)benzyl]amino}sulfonyl)benzoic acid or pharmaceutically acceptable salt thereof is administered once daily.

19. The method according to claim 17, wherein the 4-({(4-cyclopropylisoquinolin-3-yl)[4-(trifluoromethoxy)benzyl]amino}sulfonyl)benzoic acid or pharmaceutically acceptable salt thereof is administered twice daily.

20. The method according to claim 1, wherein the daily dose of the 4-({(4-cyclopropylisoquinolin-3-yl)[4-(trifluoromethoxy)benzyl]amino}sulfonyl)benzoic acid or pharmaceutically acceptable salt thereof is administered with an additional active agent.

21. The method according to claim 1, wherein the 4-({(4-cyclopropylisoquinolin-3-yl)[4-(trifluoromethoxy)benzyl]amino}sulfonyl)benzoic acid or pharmaceutically acceptable salt thereof is administered in a composition, and the composition comprises a pharmaceutically acceptable carrier.

22. The method according to claim 21, wherein the composition is a pharmaceutical composition.

23. A pharmaceutical composition comprising an amount of 4-{(4-cyclopropylisoquinolin-3-yl)[4-(trifluoromethoxy)benzyl]amino}sulfonyl) benzoic acid or a pharmaceutically acceptable salt thereof ranging from 1 mg to 10 mg and a pharmaceutically acceptable carrier, wherein the composition treats vasomotor symptoms in a subject in need thereof.

24. The pharmaceutical composition according to claim 23, further comprising an additional active agent.

* * * * *